US010119935B2

United States Patent
Trainoff

(10) Patent No.: US 10,119,935 B2
(45) Date of Patent: Nov. 6, 2018

(54) METHOD FOR THE FABRICATION OF CORROSION RESISTANT ELECTRODES

(71) Applicant: Wyatt Technology Corporation, Goleta, CA (US)

(72) Inventor: Steven P. Trainoff, Goleta, CA (US)

(73) Assignee: WYATT TECHNOLOGY CORPORATION, Goleta, CA (US)

( * ) Notice: Subject to any disclaimer, the term of this patent is extended or adjusted under 35 U.S.C. 154(b) by 156 days.

(21) Appl. No.: 15/130,762

(22) Filed: Apr. 15, 2016

(65) Prior Publication Data
US 2016/0231273 A1 Aug. 11, 2016

Related U.S. Application Data

(62) Division of application No. 14/169,008, filed on Jan. 30, 2014, now abandoned.
(Continued)

(51) Int. Cl.
| | |
|---|---|
| *G01N 27/447* | (2006.01) |
| *B23K 15/00* | (2006.01) |
| *B44C 1/22* | (2006.01) |
| *C25D 9/06* | (2006.01) |
| *B23K 103/18* | (2006.01) |

(52) U.S. Cl.
CPC ... *G01N 27/44765* (2013.01); *B23K 15/0093* (2013.01); *C25D 9/06* (2013.01); *G01N 27/44704* (2013.01); *G01N 27/44713* (2013.01); *B23K 2203/18* (2013.01)

(58) Field of Classification Search
None
See application file for complete search history.

(56) References Cited

U.S. PATENT DOCUMENTS

| | | | | | |
|---|---|---|---|---|---|
| 3,115,702 | A | * | 12/1963 | Bourne | B23K 20/233 228/214 |
| 4,443,295 | A | * | 4/1984 | Radigan | C23F 1/10 134/2 |

(Continued)

FOREIGN PATENT DOCUMENTS

| | | |
|---|---|---|
| GB | 1253217 A | 11/1971 |
| WO | 2013/022795 A1 | 2/2014 |

OTHER PUBLICATIONS

Josowicz, et.al., J. Electrochemical Society, 1988, pp. 112-115, vol. 135, Issue 1, USA.

*Primary Examiner* — Shamim Ahmed
(74) *Attorney, Agent, or Firm* — Leonard T. Guzman

(57) ABSTRACT

An electrode for use in instruments capable of measuring the electrophoretic mobility of particles in solution is disclosed. The electrode is comprised of an inexpensive support member, generally made of titanium, onto a flat surface of which has been connected, generally by microwelding, a flat electrically conductive but chemically inert foil member, preferably platinum. A uniform texture can be generated on the exposed surfaces of the electrode by various means including tumbling the electrode with an abrasive. An oxide layer can be generated on the support member by soaking the composite electrode in an appropriate medium, protecting the exposed surface of the support member from fluid contact with the sample solution, while the foil member, unaffected by the oxidation process, is able to contact the sample solution.

9 Claims, 2 Drawing Sheets

Related U.S. Application Data

(60) Provisional application No. 61/759,207, filed on Jan. 31, 2013.

(56) References Cited

U.S. PATENT DOCUMENTS

| | | |
|---|---|---|
| 4,534,937 A | 8/1985 | Meunier |
| 4,995,550 A | 2/1991 | Appl et al. |
| 5,082,543 A | 1/1992 | Gnann |
| 6,222,371 B1 | 4/2001 | Snyder |
| 6,569,300 B1 | 5/2003 | Assenmacher |
| 7,887,681 B2 | 2/2011 | Zhou |
| 8,441,638 B2 | 5/2013 | Hsieh |
| 8,525,991 B2 | 9/2013 | Hsieh |
| 2004/0251129 A1 | 12/2004 | Mundheim |
| 2005/0287758 A1* | 12/2005 | Kim ................. H01L 28/84 |
| | | 438/393 |
| 2007/0116890 A1 | 5/2007 | Adams |
| 2011/0048964 A1* | 3/2011 | Luebke ............. C02F 1/46104 |
| | | 205/687 |
| 2011/0188927 A1* | 8/2011 | Mizrahi ............. B23K 11/115 |
| | | 403/271 |
| 2012/0167659 A1* | 7/2012 | Besling ............. H01H 35/346 |
| | | 73/1.57 |

* cited by examiner

METHOD FOR THE FABRICATION OF CORROSION RESISTANT ELECTRODES

PRIORITY

This application is a division of U.S. patent application Ser. No. 14/169,008 filed Jan. 30, 2014, "Corrosion resistant electrodes for electrophoretic mobility measurements and method for their fabrication," which claims priority to U.S. Provisional Patent Application No. 61/759,207 filed Jan. 31, 2013.

RELATED APPLICATIONS AND PATENTS

The following patent applications relate to the measurement of the electrophoretic mobility of particles and are hereby incorporated by reference:

U.S. Pat. No. 8,441,638 B2, H.-T. Hsieh and S. Trainoff, "Apparatus to measure particle mobility in solution with scattered and unscattered light," issued May 14, 2013.

U.S. Pat. No. 8,525,991 B2, H.-T. Hsieh and S. Trainoff, "Method to measure particle mobility in solution with scattered and unscattered light," issued Sep. 3, 2013.

P.C.T. Application PCT/US12/49641, S. Trainoff, "Method and apparatus to suppress bubbles in optical measurement cells," filed Aug. 5, 2012, and claiming priority to U.S. Provisional Application 61/515,796, filed Aug. 5, 2011.

BACKGROUND

The present invention involves an innovative electrode design generally for use in instruments that measure the electrophoretic mobility of macromolecules in solution wherein the charged particles within solution are subject to an applied electric field, and their resulting motion is measured. Although the present disclosure will refer to macromolecules throughout much of its description, measurements using the inventive apparatus disclosed herein may include, more generally, all classes of small particles including emulsions, viruses, nanoparticles, liposomes, proteins, macro-ions, and any other solution constituents whose size may lie between about a half and a few thousand nanometers. Thus whenever a term such as "molecule," "macromolecule," "particle," or "macro-ion" is used, it should be understood to include all of the aforementioned solution-borne objects to be subject to some form of optical measurement.

Electrophoretic mobility is the directly measurable and most widely used quantity to characterize the charge of molecules, or other particles in solution. Once measured, the electrophoretic mobility can be used in turn to determine the effective charge, Ze, carried by such molecules as well as their so-called zeta potential. The interface between the group of ions tightly bound to the particle and those of the surrounding solution that do not move with the particle defines the hydrodynamic shear plane. The zeta potential represents the electrostatic potential existing at this shear plane. It is an objective of the present invention to improve the reliability of measurements of electrophoretic mobility, effective charge, and zeta potential of molecules and particles in solution contained within a measurement cell, as well as to improve the durability of the instruments and their components.

Several techniques have been developed and are available for measuring mobilities including light scattering methods such as heterodyne DLS including both laser Doppler electrophoresis, LDE, and phase analysis light scattering, PALS. These techniques involve measuring light scattered from moving particles, whereby such scattered light carries information relating to such motion and from which the associated electrophoretic mobility of the particles may be determined.

Instruments that measure electrophoretic mobility must, by necessity, apply an electrical field, generally between two electrodes, in a fluid sample to induce electrophoresis. The resulting motion is generally probed optically to determine the resulting sample velocity. This compromises a first principles measurement of mobility, which is well established as an important parameter for predicting the stability of colloidal suspensions. In recent years electrophoretic mobility is finding new use in determining the stability of molecular solutions. Over the years, many electrode designs have been used. An objective of the present invention is to provide an inexpensive electrode that applies a uniform field and is mechanically and chemically durable.

A BRIEF DESCRIPTION OF THE DRAWINGS

A DETAILED DESCRIPTION OF THE INVENTION

Figure 1:
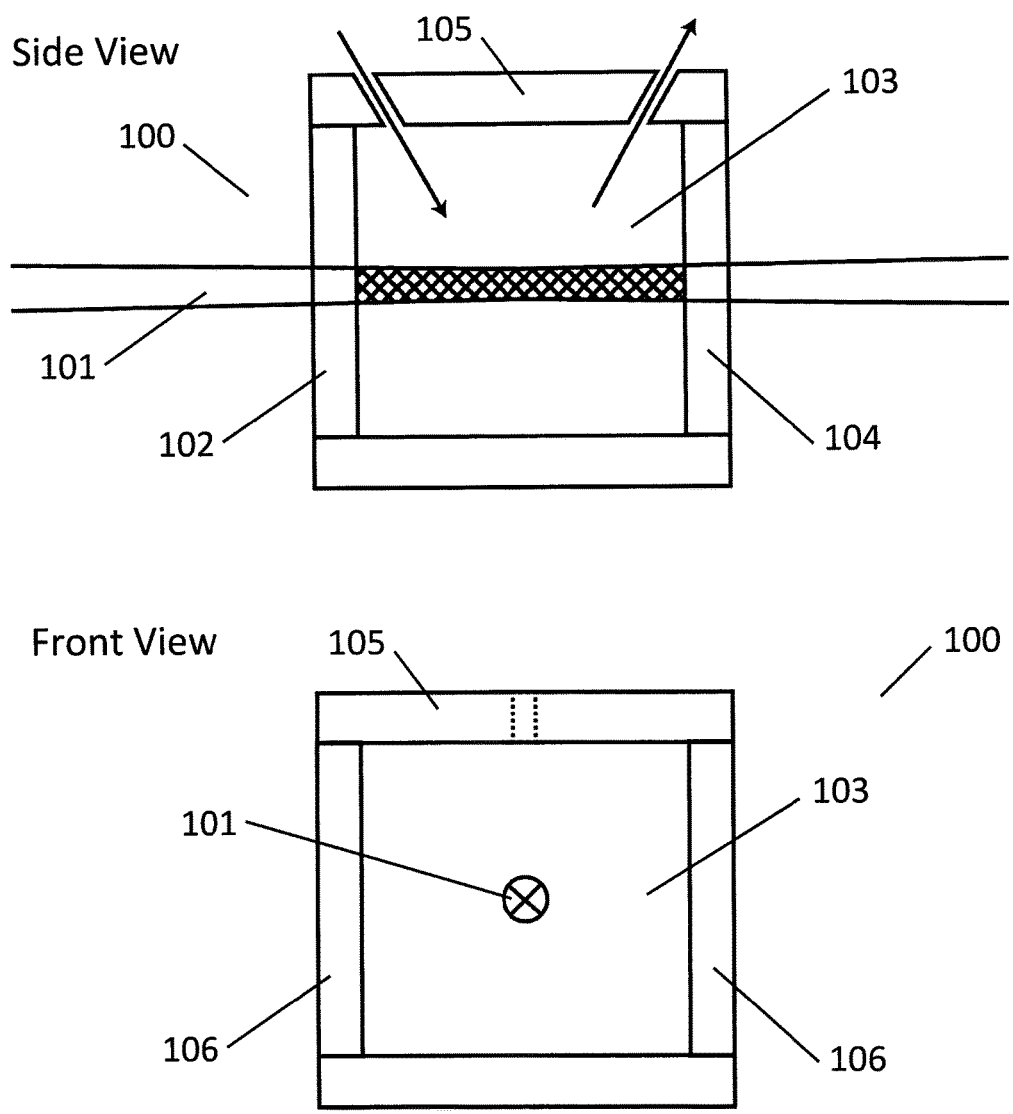
FIG. 1 shows the front and side view of an exemplar optical cell for measurement of electrophoretic mobility.

As discussed above, electrophoretic mobility measurement instruments generally employ two electrodes comprising planar surfaces placed parallel to each other, between which is placed a liquid sample and across which an electric field is generated. The applied electric field induces electrophoresis within the fluid sample. A graphic representation of the elements of an optical electrophoretic mobility measurement cell 100 is shown in FIG. 1. A beam of light 101, typically generated by a laser, passes through an optically transparent window 102 and into a sample chamber 103, wherein a fluid sample has been placed, generally through injection ports within the top plate 105. The beam leaves the chamber through exit window 104, and the physical properties of the sample molecules are derived based on measurements of the emerging beam and light scattered therefrom. The necessary electric field is generated between electrodes 106. It should be noted that many variations on this optical measurement cell exist, and the utility of the present invention is not limited to use with only a flow through system such as that shown in FIG. 1. One example of a measurement chamber for which the present invention may be advantageous is a sample cuvette containing the necessary elements of the measurement cell. The measurement chamber of the cuvette may be filled with sample prior to the cuvette being placed within the instrument itself, and thereby the sample is placed in the path of the beam. While the particular elements of the instruments and measurement cells with which the present invention may be utilized may vary, this disclosure is concerned primarily with the electrodes used to generate the electric field within these cells.

For many years platinum has been the preferred material for electrode manufacture because it is chemically inert, even in high salt buffers, and does not oxidize. Pure platinum however, is very expensive so there is a strong incentive to minimize the amount of material that is used. A common strategy is to fabricate the electrodes out of an inexpensive material, such as stainless steel, and then protect them with an electroplated platinum coating. This technique is effective, but suffers from a number of problems. In order to get good adhesion, the substrate must be exceptionally clean. Even a small amount of contamination on the surface or in the plating baths can give rise to coatings that crack or flake off. Even when extreme caution is taken to insure good adhesion, the resulting platinum coating is brittle. If the coating is made more than about 2-5 µm thick, the mechanical strain that develops during the coating process frequently causes the film to crack, exposing the underlying substrate. If the coating is made less than 2 µm thick, it may be porous, again exposing the substrate. Also, when an electrical field is applied, the underlying substrate can corrode causing the plated surface to loosen. Further, when the electrodes are cleaned, either chemically, or by gentle mechanical abrasion, the coating can detach from the substrate surface. It is therefore of critical importance that plated surfaces, with their attendant chemical and mechanical problems, be avoided in the fabrication of electrodes.

The present invention involves an innovative electrode design and its method of manufacture, which, in its various embodiments, offers the advantages of a planar surface in contact with the sample fluid which is less prone corrosion than electrodes created by standard electroplating techniques. In one embodiment this is achieved by microwelding a platinum foil surface to a support made of a less expensive material such as titanium. More specialized embodiments aid in the prevention of bubble formation on the electrode surfaces and limit the surfaces of the electrode in contact with the fluid to the planar electrode surface.

Figure 2:
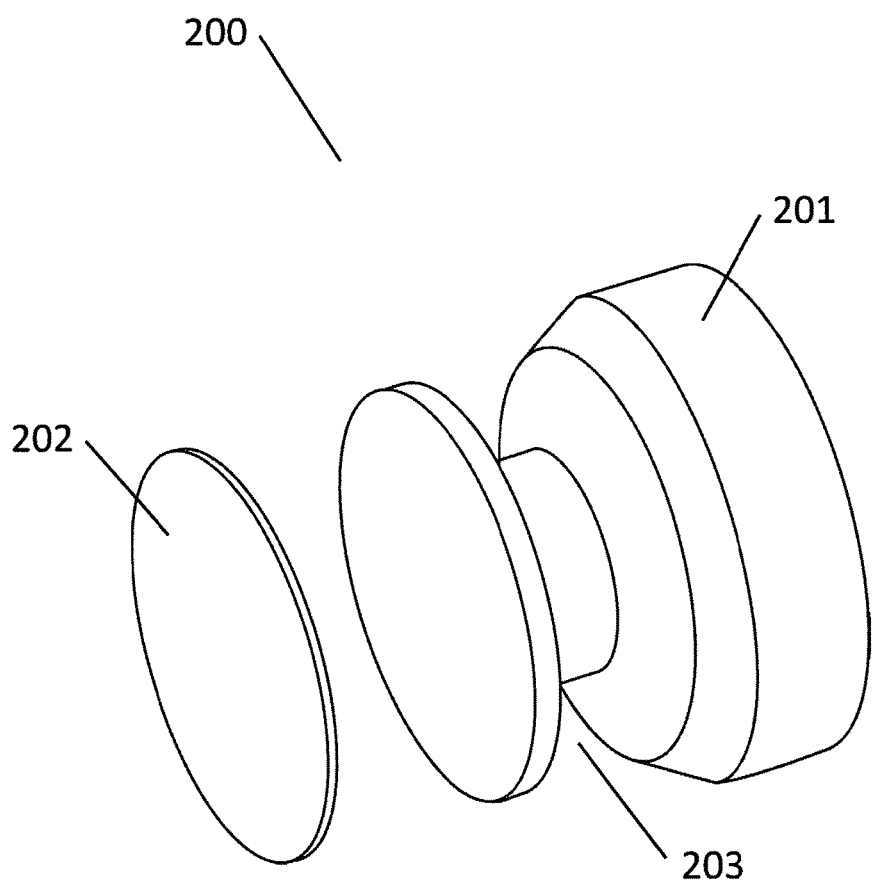
FIG. 2 illustrates the elements of an embodiment of the invention with a platinum foil member to be microwelded onto a titanium support member.

In one embodiment of the invention whose elements are shown in FIG. 2, the electrode 200 is comprised of a support member 201 made of an appropriate, but relatively inexpensive material such as titanium onto which is welded a disc of bulk conductive foil 202. This microwelding around the perimeter of the platinum foil may be performed by an electron beam. The use of electron beams to microweld surfaces is well known in the art. An o-ring groove 203 and other physical elements may be present as part of the support member. While platinum is a preferred material for this foil surface, the invention should not be limited thereto. Other chemically inert but electrically conductive materials such as gold or various alloys capable of being microwelded to a support member may also be used. As regards to platinum, or other expensive materials, it is clear that the cost of a thin foil microwelded to an inexpensive support member is far less than that of an electrode composed of solid platinum. The inventive design thus offers a considerable cost savings while still providing the benefits of a platinum electrode.

The foil surface itself can be made as thick as desired to insure mechanical robustness while still minimizing the amount of material consumed. In a preferred embodiment, the platinum foil is roughly 100 µm thick, insuring that it can be cleaned with mild abrasives without damage.

One limitation of using bulk foils is that they are generally formed by extrusion through rollers giving rise to a smooth surface with small scratches. These scratches can act as nucleation sites for electrolysis bubbles that are often formed during the measurement of samples in high conductivity solutions. To minimize the formation of bubbles, a uniform surface texture is preferred. This limitation can be overcome with another embodiment of the invention, wherein the electrode is etched after welding. Several methods can be used to achieve the desired surface etching. For example, the application hydrofluoric acid or ion beam etching may be employed. In a preferred embodiment, the etching is achieved by mechanical tumbling with an abrasive. An advantage of mechanical tumbling is that it is possible to adjust the tumbling time and abrasive bead size to easily control the final surface finish.

One limitation of some embodiments of the invention described above is that both the platinum foil and titanium support member are in contact with the fluid sample. In order to apply a uniform field, it is desirable that only the parallel plates formed by the platinum foil are in contact with the sample. This can be achieved with another embodiment of the invention wherein the composite electrode is soaked in a strong oxidizer that causes an oxide layer to grow on the exposed surfaces of the support member but wherein the platinum foil is unaffected. A preferred method for achieving this oxidation layer on the support member is the soaking of the composite electrode in a solution of 30% hydrogen peroxide in water. The oxide layer may additionally be generated with other oxidizers or electrochemically, by passing current through the electrode while bathed in a salt solution. The resulting electrode is inexpensive, chemically inert, and mechanically robust.

As will be evident to those skilled in the arts of materials science and optical and electrophoretic mobility measurements, there are many obvious variations of the methods and devices of the invention and method for manufacture thereof that do not depart from the fundamental elements that disclosed herein; all such variations are but obvious implementations of the described invention and are included by reference to our claims, which follow.

The invention claimed is:

1. A method comprising:
  providing an electrically conductive support member comprising at least one planar surface;
  providing a flat, chemically inert, electrically conductive foil member;
  welding the foil member to the conductive support member about the perimeter of the foil member, forming, thereby, a composite electrode, wherein the welding is performed by an electron beam;
  etching an exposed surface of the foil member of the composite electrode so as to achieve a uniform, non-smooth surface there upon, wherein the etching comprises mechanically tumbling the composite electrode with an abrasive; and
  in response to the etching, exposing the composite electrode to an oxidation agent, thereby causing an oxide layer to be formed upon an exposed surface of the support member.

2. The method of claim 1 wherein the foil member comprises platinum.

3. The method of claim 2 wherein the foil member is a disc of platinum foil.

4. The method of claim 3 further comprising milling an o-ring groove about a perimeter of the support member wherein the perimeter of the support member is chosen such that the perimeter does not intersect the planar surface to which the foil member is attached.

5. The method of claim 2 wherein the foil member is 100±5 µm thick, permitting thereby the foil member to be cleaned with mild abrasives without damage.

6. The method of claim 1 further comprising:
  selecting the support member to be composed of a material or materials whose surface, when exposed to a strong oxidizer, causes an oxide layer to grow thereupon; and
  selecting the foil member to be composed of a material or materials whose surface, when exposed to a strong oxidizer, resists an oxide layer forming thereupon.

7. The method of claim 1 wherein the oxidizing agent is a solution comprising hydrogen peroxide and water.

8. The method of claim 7 wherein the solution consists of 30% hydrogen peroxide and 70% water.

9. The method of claim 6 further comprising passing an electrical current through the composite electrode while the composite electrode is bathed in a salt solution, resulting in an oxide layer to form upon the support member of the composite electrode.

\* \* \* \* \*